United States Patent
Dayton et al.

(10) Patent No.: US 10,849,663 B2
(45) Date of Patent: Dec. 1, 2020

(54) BONE CUTTING GUIDE SYSTEMS AND METHODS

(71) Applicant: Treace Medical Concepts, Inc., Ponte Vedra Beach, FL (US)

(72) Inventors: Paul Dayton, Fort Dodge, IA (US); Joe William Ferguson, Ponte Vedra Beach, FL (US); F. Barry Bays, Collierville, TN (US); John T. Treace, Ponte Vedra Beach, FL (US); W. Bret Smith, Lexington, SC (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 402 days.

(21) Appl. No.: 15/210,497

(22) Filed: Jul. 14, 2016

(65) Prior Publication Data

US 2017/0014143 A1 Jan. 19, 2017

Related U.S. Application Data

(60) Provisional application No. 62/192,290, filed on Jul. 14, 2015.

(51) Int. Cl.
  *A61B 17/80* (2006.01)
  *A61B 17/15* (2006.01)
  *A61B 17/56* (2006.01)

(52) U.S. Cl.
  CPC .......... *A61B 17/8061* (2013.01); *A61B 17/15* (2013.01); *A61B 17/151* (2013.01); *A61B 2017/564* (2013.01)

(58) Field of Classification Search
  CPC ....... A61B 17/15; A61B 17/16; A61B 17/157; A61B 17/155; A61B 17/151; A61B 2017/565; A61F 2/4225
  See application file for complete search history.

(56) References Cited

U.S. PATENT DOCUMENTS

| | | |
|---|---|---|
| 3,664,022 A | 5/1972 | Small |
| 4,069,824 A | 1/1978 | Weinstock |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

(Continued)

*Primary Examiner* — David W Bates
(74) *Attorney, Agent, or Firm* — Fredrikson & Byron, P.A.

(57) ABSTRACT

A bone cutting guide may include a support that contains a shaft movable relative to the support. The shaft may carry a guide member having one or more cut guides through which a clinician inserts a cutting member to cut bone positioned under the guide cut guides. In operation, a clinician may fixate the support of the bone cutting guide to a bone and translate the guide member until the one or more cut guides are positioned at a desired cut location. The clinician may then perform a cut through the cut guide.

14 Claims, 13 Drawing Sheets

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A * | 11/1994 | Mumme ............... A61B 17/157 606/88 |
| 5,374,271 A * | 12/1994 | Hwang ............... A61B 17/1725 606/62 |
| 5,413,579 A | 5/1995 | Du Toit |
| 5,417,694 A * | 5/1995 | Marik .................. A61B 17/155 606/88 |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,601,565 A * | 2/1997 | Huebner ............... A61B 17/15 606/79 |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | McGuire |
| 6,030,391 A * | 2/2000 | Brainard ............... A61B 17/15 606/82 |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,478,799 B1 | 11/2002 | Williamson |
| 6,511,481 B2 | 1/2003 | Von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,112,204 B2 | 9/2006 | Justin et al. |
| 7,182,766 B1 * | 2/2007 | Mogul .................. A61B 17/15 606/87 |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,083,746 B2 | 12/2011 | Novak |
| 8,123,753 B2 | 2/2012 | Dubriske |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Büscher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,652,142 B2 | 2/2014 | Geissler |

(56) References Cited

U.S. PATENT DOCUMENTS

| | | |
|---|---|---|
| 8,657,820 B2 | 2/2014 | Kubiak et al. |
| D701,303 S | 3/2014 | Cook |
| 8,672,945 B2 | 3/2014 | LaVallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| 9,522,023 B2 * | 12/2016 | Haddad ............... A61B 17/809 |
| 9,687,250 B2 * | 6/2017 | Dayton ............... A61B 17/1682 |
| 9,750,538 B2 | 9/2017 | Soffiatti et al. |
| 9,785,747 B2 | 10/2017 | Geebelen |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 * | 5/2019 | Fallin ................ A61B 17/151 |
| 10,327,829 B2 | 6/2019 | Dacosta et al. |
| 10,470,779 B2 | 11/2019 | Fallin et al. |
| 10,555,757 B2 * | 2/2020 | Dayton ............... A61B 17/6416 |
| 10,575,862 B2 * | 3/2020 | Bays ................ A61B 17/152 |
| 2002/0099381 A1 * | 7/2002 | Maroney ............... A61B 17/15 |
| | | 606/86 R |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2004/0153083 A1 * | 8/2004 | Nemec ................ A61B 17/15 |
| | | 606/86 R |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 * | 11/2007 | Weinstein ............. A61B 17/15 |
| | | 606/87 |
| 2007/0270850 A1 * | 11/2007 | Geissler ................ A61B 17/15 |
| | | 606/326 |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener |
| 2008/0147073 A1 | 6/2008 | Ammann et al. |
| 2008/0172054 A1 * | 7/2008 | Claypool ............. A61B 17/157 |
| | | 606/87 |
| 2008/0195215 A1 | 8/2008 | Morton |
| 2008/0208252 A1 | 8/2008 | Holmes |
| 2008/0262500 A1 | 10/2008 | Callazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 * | 1/2011 | Orfaly ................ A61B 17/1717 |
| | | 606/62 |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 * | 5/2012 | Iannotti ................ A61B 17/17 |
| | | 606/87 |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0296339 A1 * | 11/2012 | Iannotti ................ A61F 2/46 |
| | | 606/87 |
| 2012/0330135 A1 * | 12/2012 | Millahn ............... A61B 34/20 |
| | | 600/424 |
| 2013/0012949 A1 | 1/2013 | Fallin et al. |
| 2013/0035694 A1 | 2/2013 | Grimm et al. |
| 2013/0085499 A1 | 4/2013 | Lian |

(56) References Cited

U.S. PATENT DOCUMENTS

| | | | |
|---|---|---|---|
| 2013/0096563 A1* | 4/2013 | Meade | A61B 17/154 606/88 |
| 2013/0131821 A1 | 5/2013 | Cachia | |
| 2013/0150903 A1 | 6/2013 | Vincent | |
| 2013/0158556 A1* | 6/2013 | Jones | A61B 17/157 606/87 |
| 2013/0165936 A1 | 6/2013 | Myers | |
| 2013/0165938 A1 | 6/2013 | Chow et al. | |
| 2013/0172942 A1 | 7/2013 | Lewis et al. | |
| 2013/0184714 A1 | 7/2013 | Kaneyama et al. | |
| 2013/0190765 A1 | 7/2013 | Harris et al. | |
| 2013/0190766 A1 | 7/2013 | Harris et al. | |
| 2013/0204259 A1 | 8/2013 | Zajac | |
| 2013/0226248 A1 | 8/2013 | Hatch et al. | |
| 2013/0226252 A1 | 8/2013 | Mayer | |
| 2013/0231668 A1 | 9/2013 | Olsen et al. | |
| 2013/0237987 A1 | 9/2013 | Graham | |
| 2013/0237989 A1 | 9/2013 | Bonutti | |
| 2013/0267956 A1 | 10/2013 | Terrill et al. | |
| 2013/0310836 A1 | 11/2013 | Raub et al. | |
| 2013/0325019 A1 | 12/2013 | Thomas et al. | |
| 2013/0325076 A1 | 12/2013 | Plamer et al. | |
| 2013/0331845 A1 | 12/2013 | Horan et al. | |
| 2013/0338785 A1 | 12/2013 | Wong | |
| 2014/0005672 A1 | 1/2014 | Edwards et al. | |
| 2014/0025127 A1 | 1/2014 | Richter et al. | |
| 2014/0039501 A1 | 2/2014 | Schickendantz et al. | |
| 2014/0039561 A1 | 2/2014 | Weiner et al. | |
| 2014/0046387 A1 | 2/2014 | Waizenegger | |
| 2014/0074099 A1 | 3/2014 | Vigneron et al. | |
| 2014/0074101 A1 | 3/2014 | Collazo | |
| 2014/0094861 A1 | 4/2014 | Fallin | |
| 2014/0094924 A1 | 4/2014 | Hacking et al. | |
| 2014/0135775 A1 | 5/2014 | Maxson et al. | |
| 2014/0163563 A1 | 6/2014 | Reynolds et al. | |
| 2014/0171953 A1 | 6/2014 | Gonzalvez et al. | |
| 2014/0180342 A1 | 6/2014 | Lowery et al. | |
| 2014/0188139 A1 | 7/2014 | Fallin et al. | |
| 2014/0194884 A1 | 7/2014 | Martin et al. | |
| 2014/0194999 A1 | 7/2014 | Orbay et al. | |
| 2014/0207144 A1 | 7/2014 | Lee et al. | |
| 2014/0249537 A1 | 9/2014 | Wong et al. | |
| 2014/0257308 A1 | 9/2014 | Johannaber | |
| 2014/0257509 A1 | 9/2014 | Dacosta et al. | |
| 2014/0276815 A1 | 9/2014 | Riccione | |
| 2014/0276853 A1 | 9/2014 | Long et al. | |
| 2014/0277176 A1 | 9/2014 | Buchanan et al. | |
| 2014/0277214 A1 | 9/2014 | Helenbolt et al. | |
| 2014/0288562 A1 | 9/2014 | Von Zabern et al. | |
| 2014/0296995 A1 | 10/2014 | Reiley et al. | |
| 2014/0303621 A1 | 10/2014 | Gerold et al. | |
| 2014/0336658 A1 | 11/2014 | Luna et al. | |
| 2014/0343555 A1 | 11/2014 | Russi et al. | |
| 2015/0032168 A1 | 1/2015 | Orsak et al. | |
| 2015/0045801 A1* | 2/2015 | Axelson, Jr. | A61B 17/155 606/88 |
| 2015/0045839 A1 | 2/2015 | Dacosta et al. | |
| 2015/0051650 A1 | 2/2015 | Verstreken et al. | |
| 2015/0057667 A1 | 2/2015 | Ammann et al. | |
| 2015/0066094 A1 | 3/2015 | Prandi et al. | |
| 2015/0112446 A1 | 4/2015 | Melamed et al. | |
| 2015/0119944 A1 | 4/2015 | Geldwert | |
| 2015/0142064 A1 | 5/2015 | Perez et al. | |
| 2015/0150608 A1 | 6/2015 | Sammarco | |
| 2015/0182273 A1 | 7/2015 | Stemniski et al. | |
| 2015/0223851 A1 | 8/2015 | Hill et al. | |
| 2015/0245858 A1 | 9/2015 | Weiner et al. | |
| 2016/0015426 A1 | 1/2016 | Dayton | |
| 2016/0022315 A1 | 1/2016 | Soffiatti et al. | |
| 2016/0151165 A1 | 6/2016 | Fallin et al. | |
| 2016/0175089 A1 | 6/2016 | Fallin et al. | |
| 2016/0192950 A1 | 7/2016 | Dayton et al. | |
| 2016/0199076 A1 | 7/2016 | Fallin et al. | |
| 2016/0213384 A1 | 7/2016 | Fallin et al. | |
| 2016/0235414 A1 | 8/2016 | Hatch et al. | |
| 2016/0242791 A1 | 8/2016 | Fallin et al. | |
| 2016/0256204 A1 | 9/2016 | Patel et al. | |
| 2016/0324532 A1 | 11/2016 | Montoya et al. | |
| 2016/0354127 A1 | 12/2016 | Lundquist et al. | |
| 2017/0042598 A1 | 2/2017 | Santrock et al. | |
| 2017/0042599 A1 | 2/2017 | Bays et al. | |
| 2017/0079669 A1 | 3/2017 | Bays et al. | |
| 2017/0143511 A1 | 5/2017 | Cachia | |
| 2017/0164989 A1 | 6/2017 | Weiner et al. | |
| 2018/0344334 A1* | 12/2018 | Kim | A61B 17/1764 |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 0685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 2006158972 A | 6/2006 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B1 | 11/2014 |
| KR | 100904142 B1 | 6/2009 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |

(56) References Cited

FOREIGN PATENT DOCUMENTS

| | | |
|---|---|---|
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

Anderson et al., "Uncemented Star Total Ankle Prostheses," The Journal of Bone and Joint Surgery, vol. 86(1, Suppl 2), Sep. 2004, pp. 103-111, (Abstract Only).
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

"Lag Screw Target Bow," Stryker Leibinger GmbH & Co. KG, Germany 2004, 8 pages.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Rx-Fix Mini Rail External Fixator, Wright Medical Technology, Brochure, Aug. 15, 2014, 2 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
TempFix Spanning the Ankle Joint Half Pin and Transfixing Pin Techniques, Biomet Orthopedics, Surgical Technique, 2012, 16 pages.
Weber et al., "A Simple System for Navigation of Bone Alignment Osteotomies of the Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

(56) References Cited

OTHER PUBLICATIONS

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Talbot et al., "Assessing Sesamoid Subluxation: How Good is the AP Radiograph?," Foot and Ankle International, vol. 19, No. 8, Aug. 1998, pp. 547-554.
Yasuda et al., "Proximal Suination Osteotomy of the First Metatarsal for Hallux Valgus," Foot and Ankle International, vol. 36, No. 6, Jun. 2015, pp. 696-704.
Gregg et al., "Plantar plate repair and Weil osteotomy for metatarsophalangeal joint instability," Foot and Ankle Surgery, vol. 13, 2007, pp. 116-121.
Weil et al., "Anatomic Plantar Plate Repair Using the Weil Metatarsal Osteotomy Approach," Foot & Ankle Specialist, vol. 4, No. 3, 2011, pp. 145-150.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International Journal, vol. 32, No. 5, May 2011, pp. 567-569.
"Futura Forefoot Implant Arthroplasty Products," Tornier, Inc., 2008, 14 pages.
Gotte, "Entwicklung eines Assistenzrobotersystems für die Knieendoprothetik," Forschungsberichte, Technische Universitat Munchen, 165, 2002, 11 pages, including partial English Translation.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Halluxvalgus-Deformität mittels IVP-Plattenfixateur (V-TEK-System)," Operative Orthopädie und Traumatologie, vol. 26, No. 2, 2014, pp. 184-195, including English Abstract on p. 186.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Otsuki et al., "Developing a novel custom cutting guide for curved per-acetabular osteotomy," International Orthopaedics (SICOT), vol. 37, 2013, pp. 1033-1038.
"Patient to Patient Precision, Accu-Cut, Osteotomy Guide System," BioPro, Foot & Ankle International, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
"Smith & Nephew scores a HAT-TRICK with its entry into the high-growth hammer toe repair market," Smith & Nephew, Jul. 31, 2014, 2 pages.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Wendl et al., "Navigation in der Knieendoprothetik," OP-Journal, vol. 17, 2002, pp. 22-27, including English Abstract.
Alvine et al., "Peg and Dowel Fusion of the Proximal Interphalangeal Joint," Foot & Ankle, vol. 1, No. 2, 1980, pp. 90-94.
Bednarz et al., "Modified Lapidus Procedure for the Treatment of Hypermobile Hallux Valgus," Foot & Ankle International, vol. 21, No. 10, Oct. 2000, pp. 816-821.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al., "The Lapidus Procedure: A Prospective Cohort Outcome Study," Foot & Ankle International, vol. 25, No. 8, Aug. 2004, pp. 526-531.
Doty et al., "Hallux valgus and hypermobility of the first ray: facts and fiction," International Orthopaedics, vol. 37, 2013, pp. 1655-1660.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Lapidus, "The Author's Bunion Operation From 1931 to 1959," Clinical Orthopaedics, vol. 16, 1960, pp. 119-135.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.

\* cited by examiner

BONE CUTTING GUIDE SYSTEMS AND METHODS

RELATED APPLICATION

This application claims the benefit of U.S. Provisional Application Ser. No. 62/192,290, filed Jul. 14, 2015, the entire contents of which are hereby incorporated by reference.

TECHNICAL FIELD

This disclosure relates generally to devices and methods for cutting bones.

BACKGROUND

Bones, such as the bones of a foot, may be anatomically misaligned. In certain circumstances, surgical intervention is required to correctly align the bones to reduce patient discomfort and improve patient quality of life.

SUMMARY

In general, this disclosure is directed to bone cutting guide systems and techniques for cutting bones. In some examples, a bone cutting guide includes a support that houses a shaft that can translate relative to the support. The shaft may carry a main guide member that defines one or more cutting guide surfaces. For example, the main guide member may define opposed guide surfaces configured to receive a cutting member. In use, the cutting member may be inserted between the opposed guide surfaces and bounded within a range of movement by the guide surfaces, causing the cutting member to be directed at a cutting location under the guide surfaces. Additionally or alternatively, the main guide member may define a single cutting surface/plane. The cutting surface/plane may be a surface against which a clinician can position a cutting member and then guide the cutting member along the cutting surface/plane to perform a cutting operation.

In some configurations, the bone cutting guide includes fixation members, such as fixation pins or apertures, that allow the main body to be fixated on or adjacent a bone to be cut. For example, in use, a clinician may fixate the main body to a bone (e.g., a first metatarsal). Thereafter, the clinician may translate the main guide member having at least one cutting guide surface (e.g., opposed cutting guide surfaces) relative to the fixed main body. The clinician can translate the main guide member by sliding or rotating the shaft housed within the main body, e.g., causing the distal end of the shaft and main guide member carried thereon away from or towards the main body. Once suitably positioned, the clinician may or may not lock the location of the shaft and perform one or more cuts through the guide surfaces of the main guide member.

To perform a surgical procedure, a clinician may attach the support of the bone cutting guide to a bone. For example, the clinician may insert fixation members, such as fixation pins or screws, through apertures in the support to fixate the support to the bone (e.g., first metatarsal). Thereafter, the clinician may translate the main guide member having at least one cutting guide surface (e.g., opposed cutting guide surfaces) relative to the support. The clinician can translate the main guide member by moving a shaft housed within the inner cavity of the support, e.g., causing the distal end of the shaft and main guide member carried thereon to move away from or towards the support. Once suitably positioned, the clinician may or may not lock the location of the shaft and perform one or more cuts through the guide surfaces of the main guide member.

The details of one or more examples are set forth in the accompanying drawings and the description below. Other features, objects, and advantages will be apparent from the description and drawings, and from the claims.

DETAILED DESCRIPTION

Figure 1:
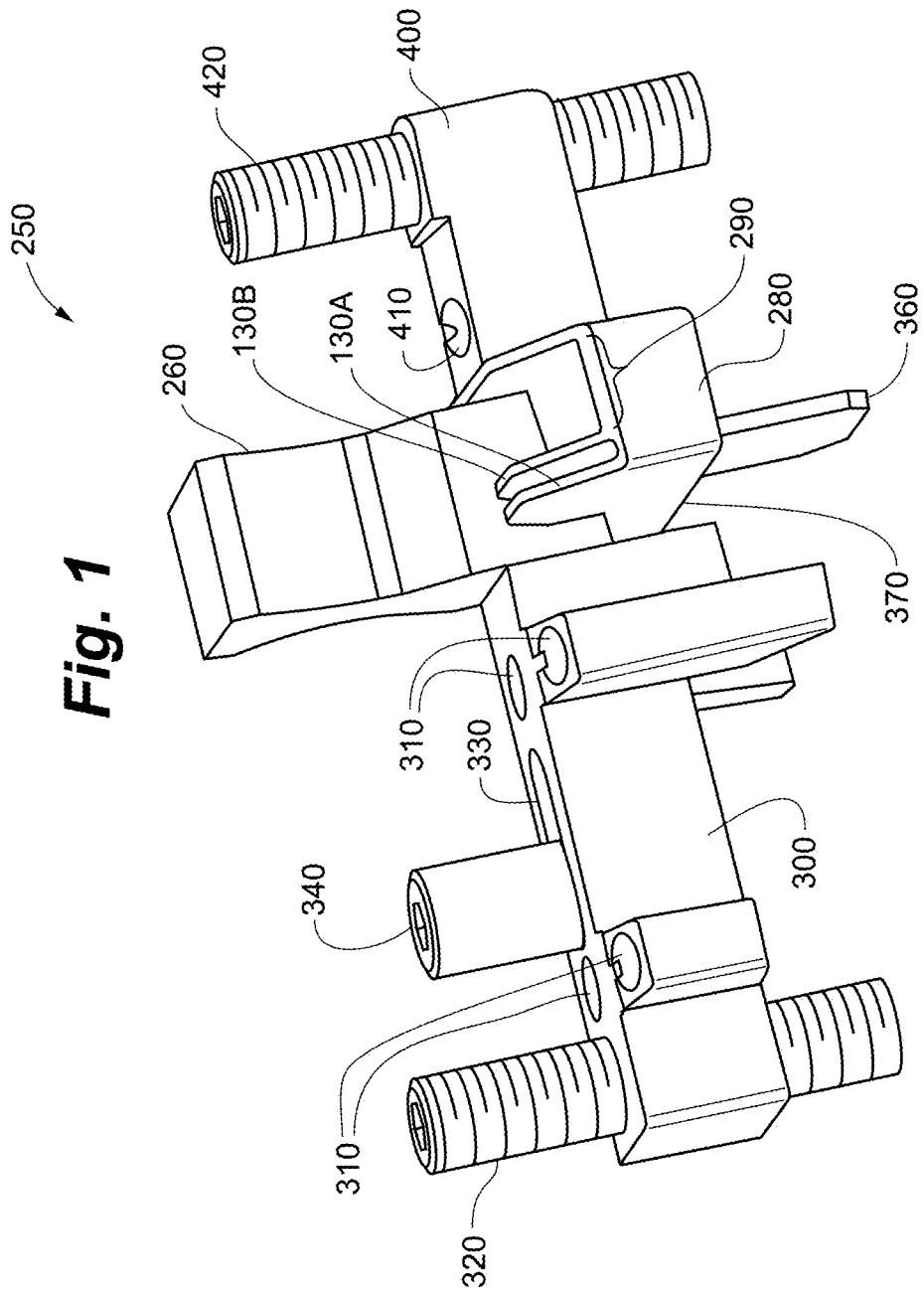
FIG. 1 is a perspective view of a bone cutting guide in accordance with an embodiment of the invention.

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the present invention include a bone cutting guide. In an exemplary application, embodiments of the bone cutting guide can be useful during a surgical procedure, such as a bone alignment, osteotomy, fusion procedure, and/or other procedures where one or more bones are to be cut. Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing the bone cutting guide can be performed to correct an alignment between a metatarsal (e.g. a first metatarsal) and a cuneiform (e.g., a first cuneiform), such as a bunion correction. An example of such a procedure is a Lapidus procedure. In another example, the procedure can be performed by modifying an alignment of a metatarsal (e.g. a first metatarsal). An example of such a procedure is a basilar metatarsal osteotomy procedure.

FIGS. 1-4 show an embodiment of a bone cutting guide 250. The bone cutting guide 250 includes a support 300 that defines an inner cavity. In one embodiment, the support 300 includes at least one fixation aperture 310 to receive at least one fixation pin. As shown, fixation apertures 310 can extend through the support 300 at a vertical angle (e.g., parallel to the longitudinal axis of the support) or a skewed angle relative to the longitudinal axis of the support (e.g., an angle ranging from 10 degrees to 55 degrees relative to the longitudinal axis of the support, such as an angle of approximately 20 degrees). In some configurations, the bone cutting guide 250 also includes an adjustable stabilization screw 320 engaged with the support 300 that can be used to stabilize the support with respect to a bone.

In the configuration of FIGS. 1-4, the bone cutting guide 250 includes a slot 330 and a securing component 340. The slot 330 is formed on and/or through at least a portion of a surface of the support 300. The securing component 340 is positioned at least partially within the slot 330 and configured to translate along the slot relative to the support 300. For example, the securing component 340 can have a first end with a diameter greater than a diameter of a second opposite end, such that the first end of the securing component 340 is supported by the slot 330 (e.g., the first end has a diameter greater than a width of the slot) while the second end of the securing component 340 is positioned within the slot (e.g., the second end has a diameter less than a width of the slot).

Figure 2:
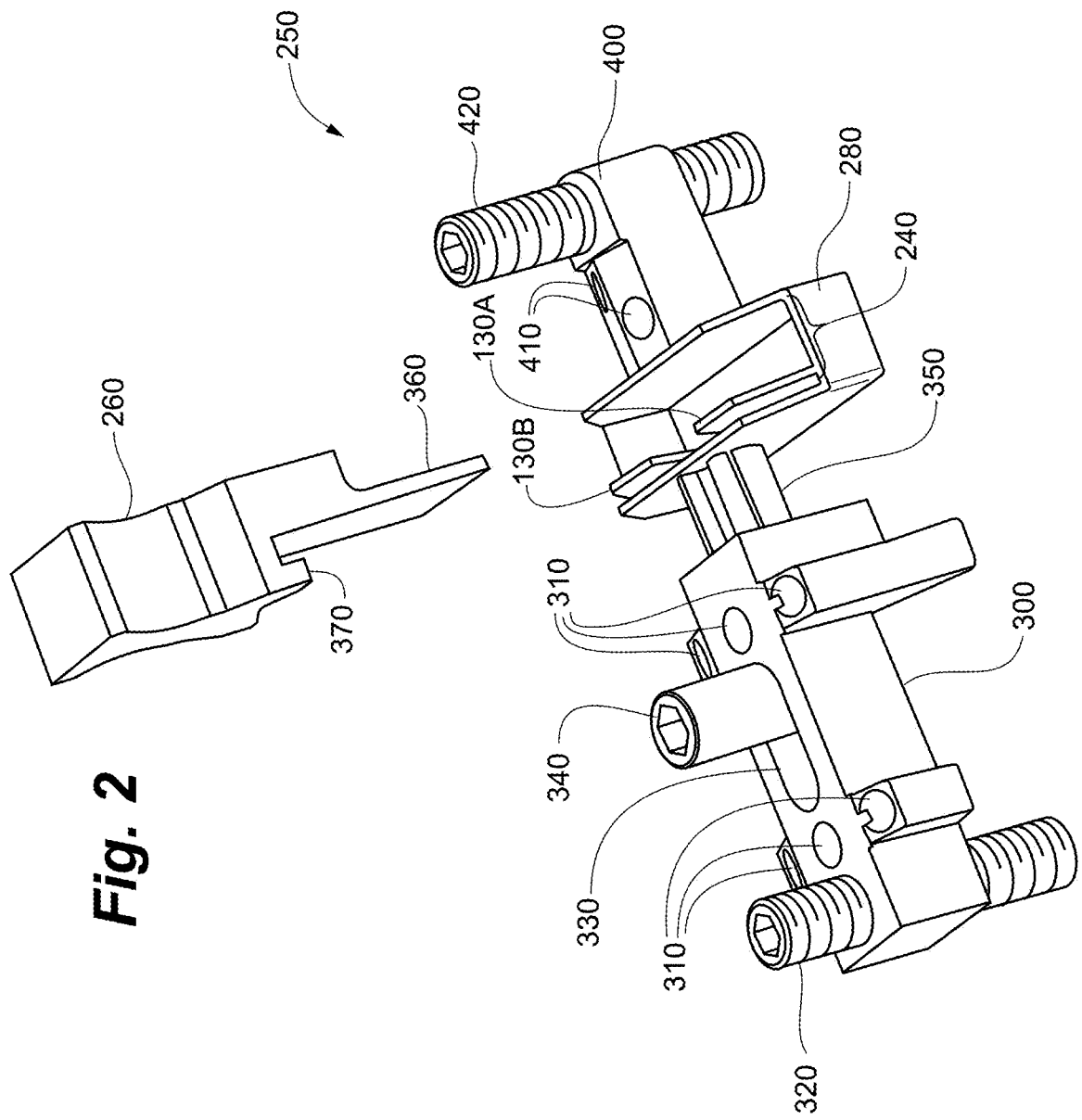
FIG. 2 is a perspective view of the bone cutting guide of FIG. 1, with a spacer detached.
Figure 3:
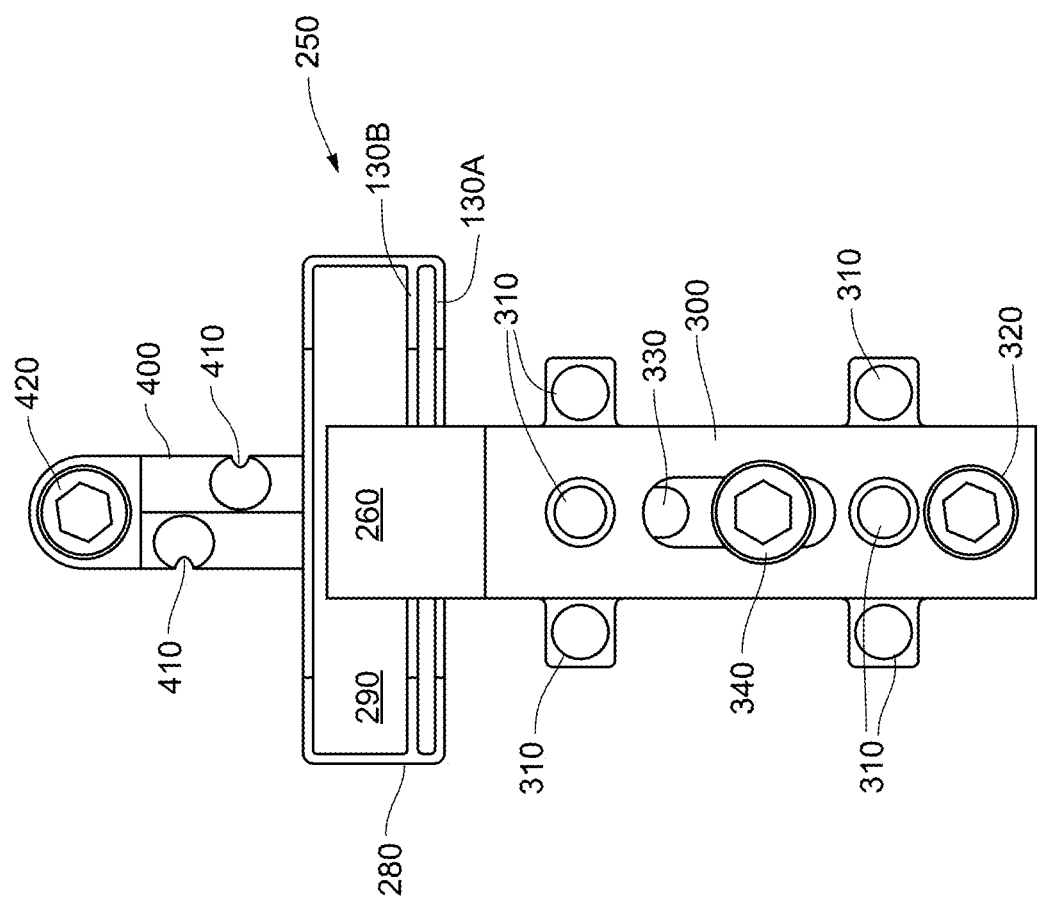
FIG. 3 is a top view of the bone cutting guide of FIG. 1.
Figure 4:
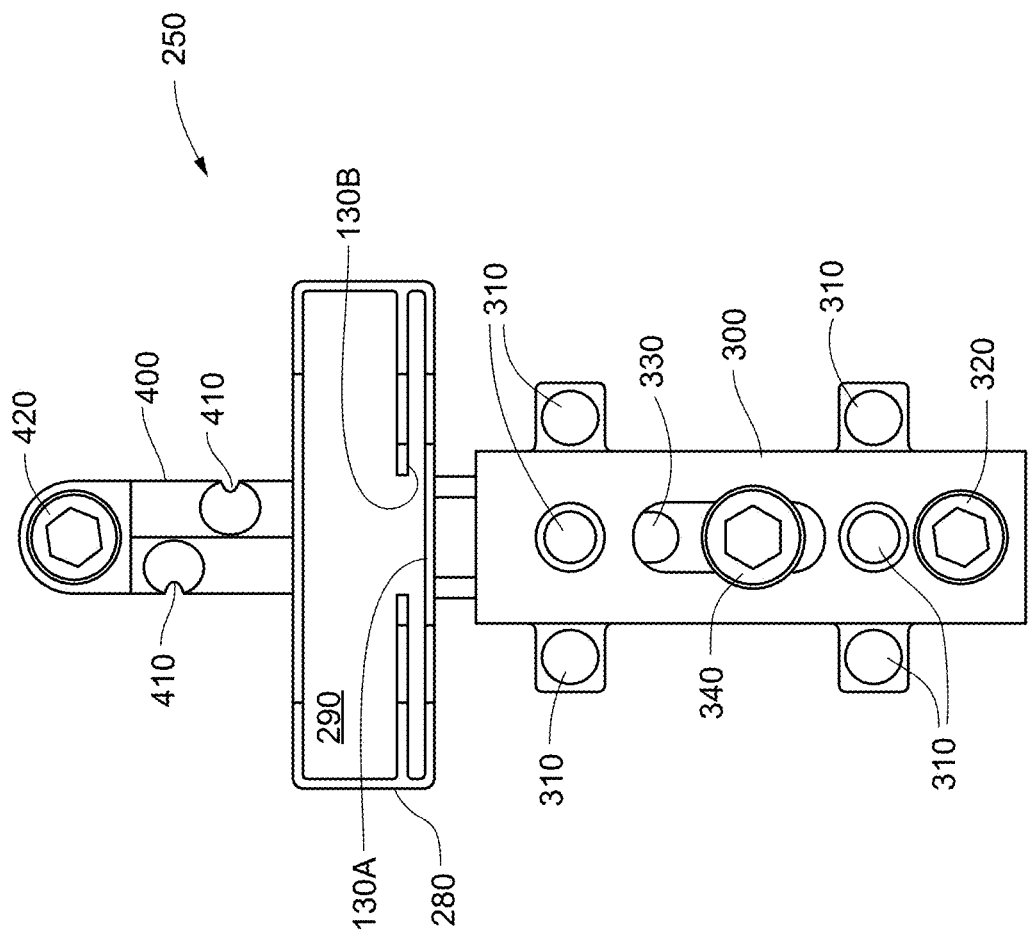
FIG. 4 is a top view of the bone cutting guide of FIG. 1, with the spacer removed.

As shown best in FIG. 2, a shaft 350 can be positioned at least partially within the inner cavity of the support 300. The shaft 350 can be configured to translate within the inner cavity relative to the support 300, such that the shaft can project out from the inner cavity and retract into the inner cavity (compare shaft position in FIG. 1 to FIG. 2). In one embodiment, the securing component 340 can be threadingly engaged with the support 300 to bear against the shaft 350 to prevent the shaft 350 from traveling with the cavity when desired.

The bone cutting guide 250 in the illustrate example includes a main guide member 280 disposed on the shaft 350. In some embodiments, the main guide member 280 can be integral with the shaft, while in other embodiments the main guide member and the shaft can be separate components coupled together. The main guide member 280 can have a first guide surface 130A and, optionally, a second guide surface 130B. The first and second guide surfaces 130A and 130B can be adjacent surfaces facing one another with a space defined between the first and second guide surfaces 130A and 130B. In use, a clinician can position a cutting member (e.g., a saw) against first guide surface 130A (e.g., between first and second guide surfaces 130A and 130B) and translate the cutting member along or through the guide surface(s). In this way, the guide surface(s) can align the cutting member with the surface of a bone to be cut.

In the illustrated embodiment, the second guide surface 130B contains a gap bisecting the planar face of the second guide surface, such that the second guide surface 130B is not a single, continuous surface. This gap can be used by the clinician to visualize the cutting member when positioned between the first and second guide surfaces 130A and 130B. In other embodiments, the second guide surface 130B can be a single, continuous surface lacking any such gap.

As shown in FIGS. 1 and 2, the first guide surface 130A may define a first plane while the second guide surface 130B may define a second plane. The first guide surface 130A and the second guide surface 130B can be arranged such that the first plane is parallel to the second plane, with the space therebetween, as shown in FIGS. 1 and 2. Alternatively, the guide surfaces can be arranged such that the first and/or second planes are skewed (e.g., non-parallel relative to each other). Additionally, in some embodiments, the main guide member 280 includes a viewing window 290 to provide a visual path to bones during cuts.

In the embodiment shown in FIGS. 1 and 2, the cutting guide 250 includes a removable spacer 260 engageable with the main guide member 280. The spacer 260 can have a first portion 360 configured to extend into a joint space (e.g., in a joint space between a first metatarsal and medial cuneiform) and a second portion 370 engageable with the main guide member 280. Such a spacer can be useful for positioning the main cut guide at a desired position with respect to a joint. Further, the first and second surfaces of the main cut guide and/or the surfaces of the spacer can be used to establish a pre-determined cut thickness.

Some embodiments of the cutting guide 250 include an anchor 400 to connect to a bone portion that is spaced from a bone portion to which the support 300 is connected. For example, cutting guide 250 may bridge a joint, fracture, or cut with the adjustable stabilization screw 320 positioned on one bone portion (e.g., a metatarsal or cuneiform) and the anchor positioned on the opposite side (e.g., the other of the metatarsal or cuneiform). In some embodiments, the anchor 400 is translatable with the shaft 350 and located along the shaft 350 on a side of the main guide member 280 opposite the support 300.

In one embodiment, the anchor 400 includes at least one fixation aperture 410 to receive at least one fixation pin. Such aperture(s) may extend through the anchor at a parallel (e.g., vertical) or skewed angle relative to the longitudinal axis of the anchor. Further, as shown, a second adjustable stabilization screw 420 can be provided to stabilize the anchor with respect to a bone. In some embodiments, after making an angular correction to a bone, the anchor 400 can be used to hold the angular orientation of the bone so that a second cut can be made parallel to the first cut.

In practice, the bone cutting guide 250 can be used to guide one or more cutting operations performed on a bone or bones. For example, the bone cutting guide 250 can be used to cut the end faces of adjacent bones to prepare the end faces (e.g., leading edges) of the bones. Such adjacent end faces can end faces of two different bones separated by a joint, or can be different portions of a single bone, separated by a fracture. In some embodiments, a clinician may attach the bone cutting guide 250 to the bone or bones to be cut then advance a cutting member along one or more guide surfaces of the bone cutting guide to cut the end faces of the one or more bones. The clinician may realign the bones relative to each other before or after the bones are cut and may also perform additional surgical steps, such as bone plating, after the cuts have been made.

Figure 5:
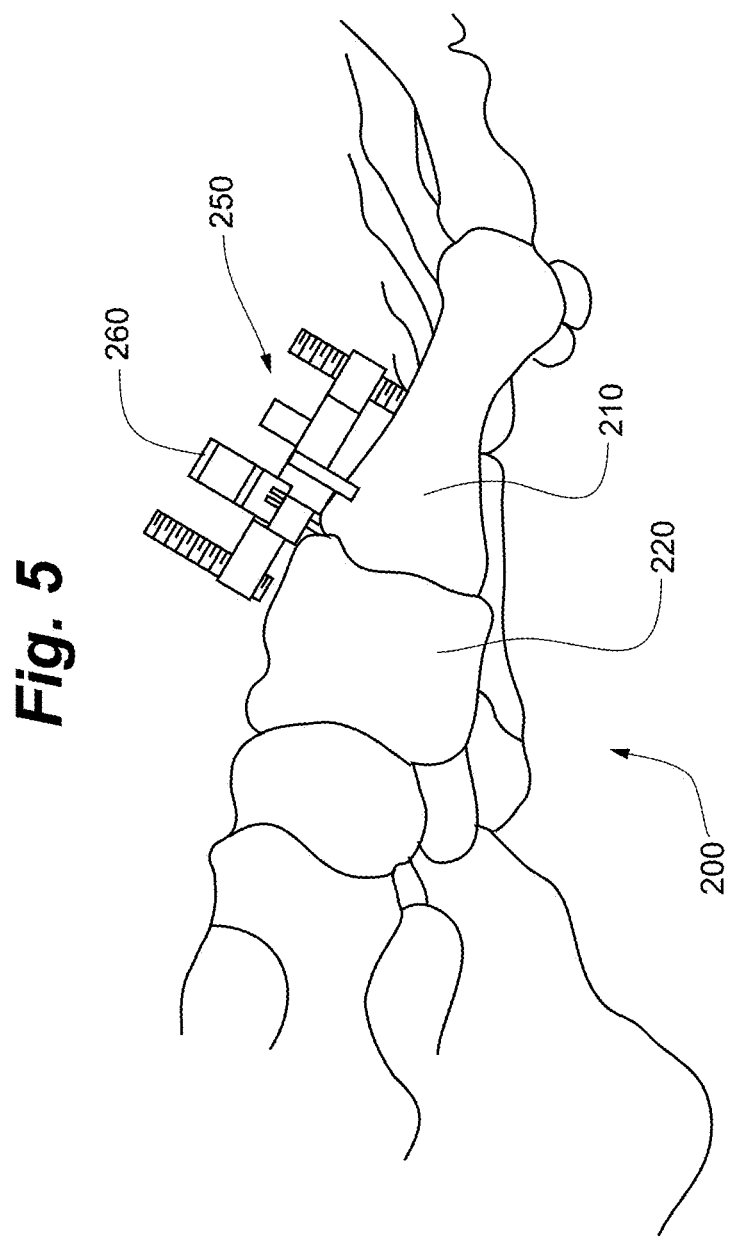
FIG. 5 is a side perspective view of a bone cutting guide on a foot in accordance with a medical procedure of an exemplary embodiment of the invention.
Figure 6:
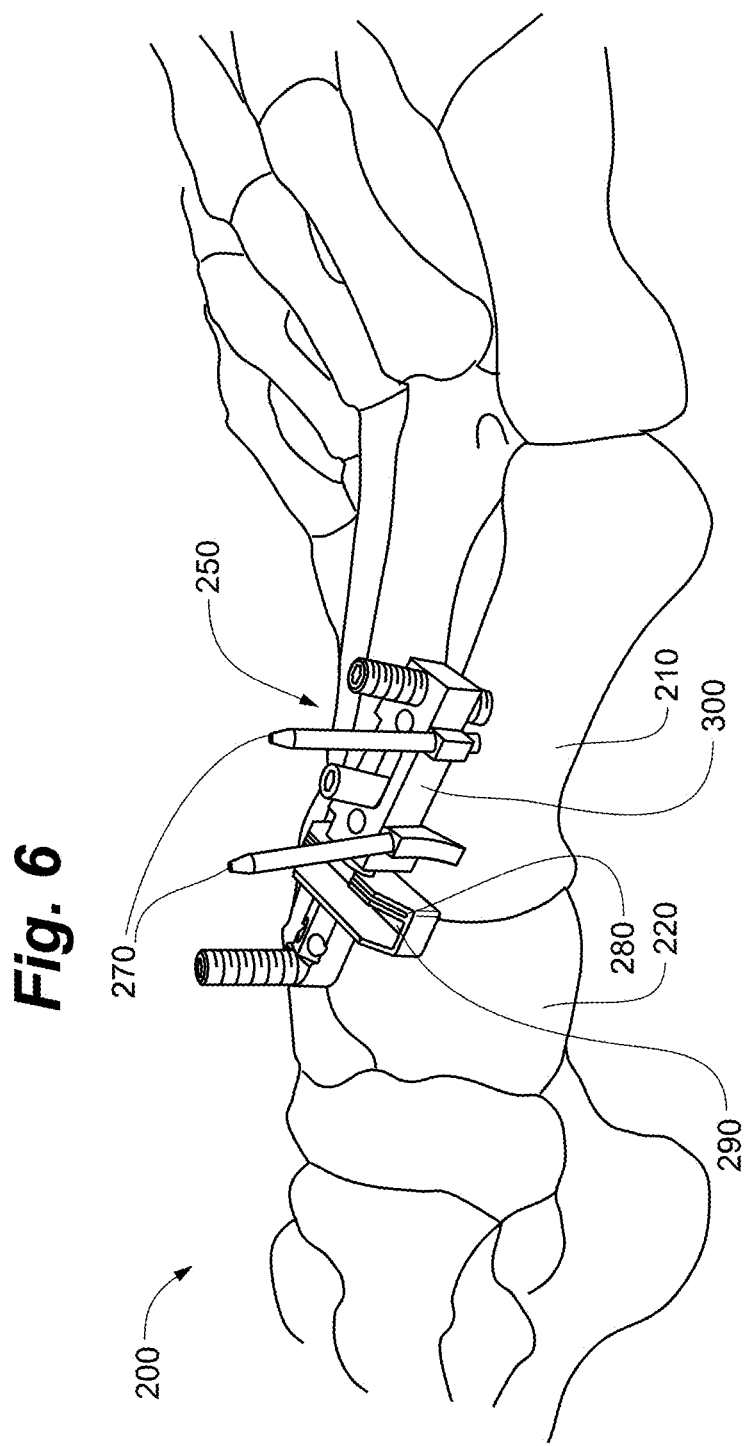
FIG. 6 is a side perspective view of a bone cutting guide on a foot held by fixation pins and positioned for a first bone cut in accordance with an embodiment of the invention.
Figure 7:
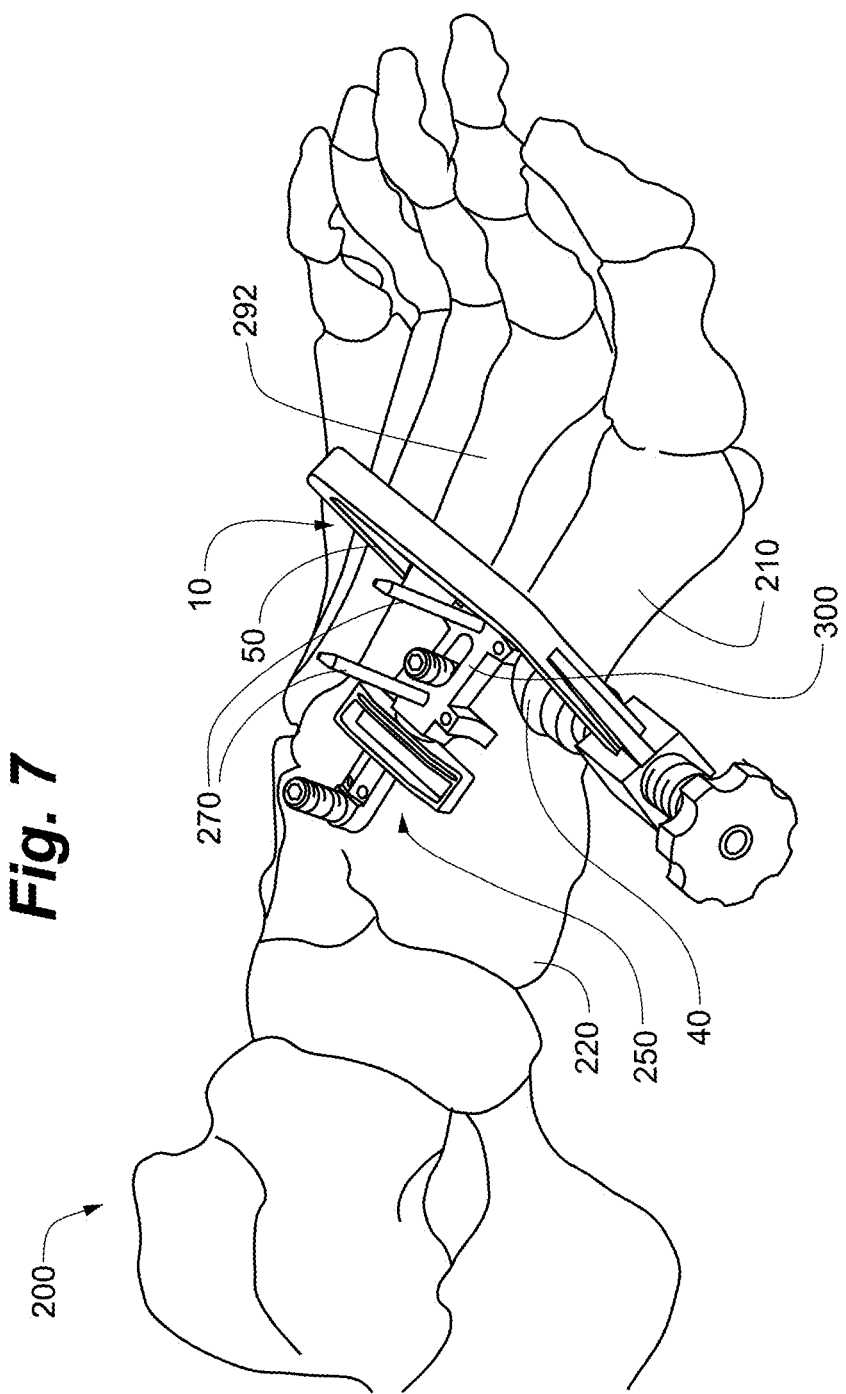
FIG. 7 is a perspective view of a bone cutting guide and a bone positioning guide on a foot in accordance with an embodiment of the invention.

FIGS. 5-13 illustrate steps of an exemplary method for cutting a bone using a bone cutting guide, such as bone cutting guide 250 described with respect to FIGS. 1-4, during a medical procedure. FIGS. 5-13 depict a foot 200 having a first metatarsal 210 and a first cuneiform 220 (medial cuneiform). In FIG. 5, the bone cutting guide 250 is positioned in longitudinal alignment with the long axis of the first metatarsal 210 and the first cuneiform 220, generally on the dorsal or dorsal-medial surface. As shown, the spacer 260 can be positioned within the joint between the first metatarsal and the first cuneiform. As shown in FIG. 6, fixation pins 270 can be inserted into the support 300 of the bone cutting guide 250 through angled apertures to fix the position of the cutting guide 250 to the first metatarsal 210 and the spacer can be removed. The end of the first metatarsal 210 facing the first cuneiform 220 can be cut with a cutting member (e.g., saw) inserted through the main guide member 280 having parallel first and second surfaces. The main guide member can also include a viewing window 290 adjacent the first and second surfaces to facilitate visualization of the cutting procedure by the clinician. The cutting guide 250 can be removed vertically from the fixation pins 270 and the bone slice removed. As shown in FIG. 7, the cutting guide 250 can be inserted back on the foot 200, such as by inserting the fixation pins 270 through vertical apertures in support 300.

Figure 8:
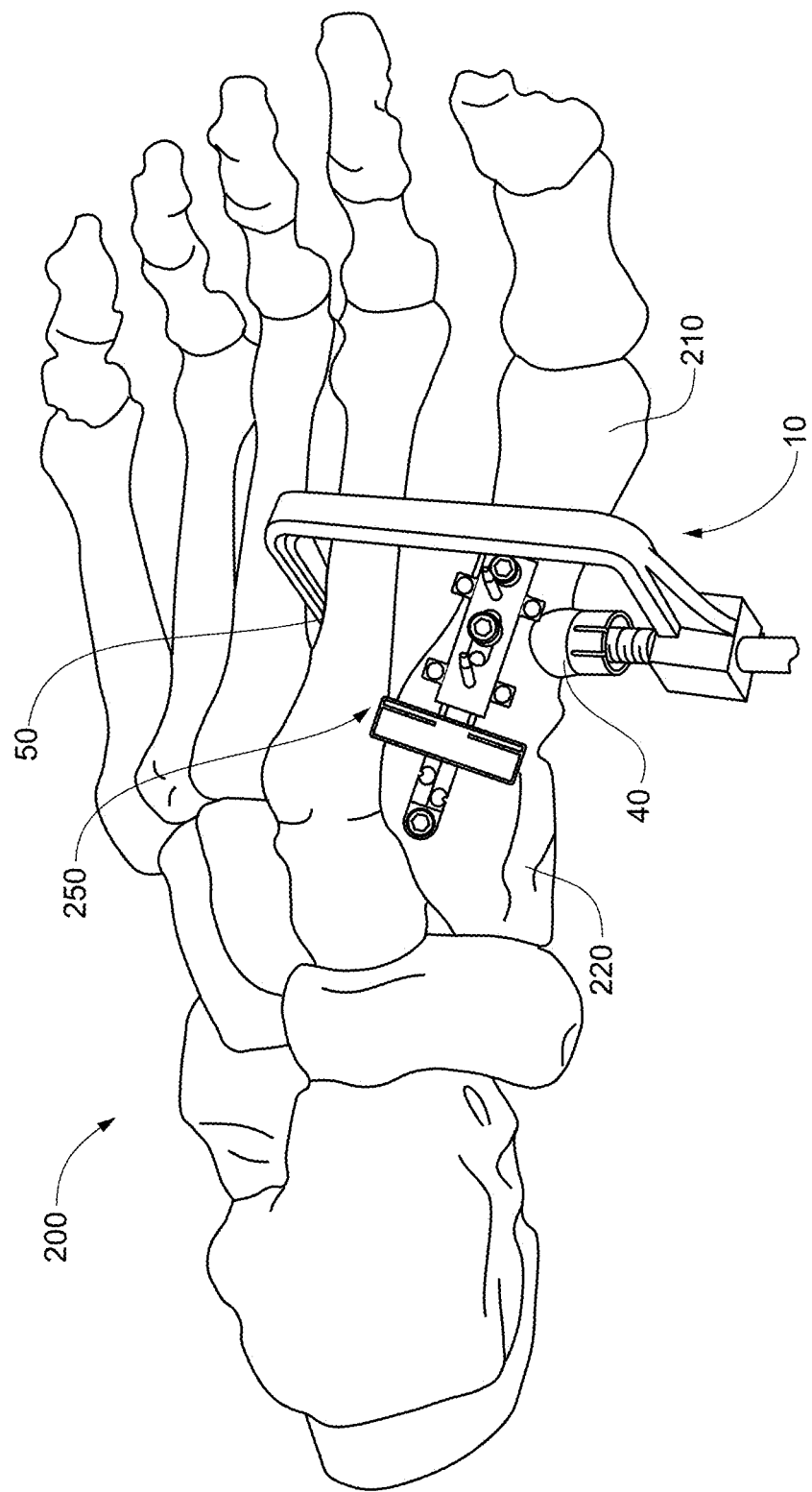
FIG. 8 is a perspective view of a bone cutting guide and a bone positioning guide on a foot depicting a bone adjustment in accordance with an embodiment of the invention.
Figure 9:
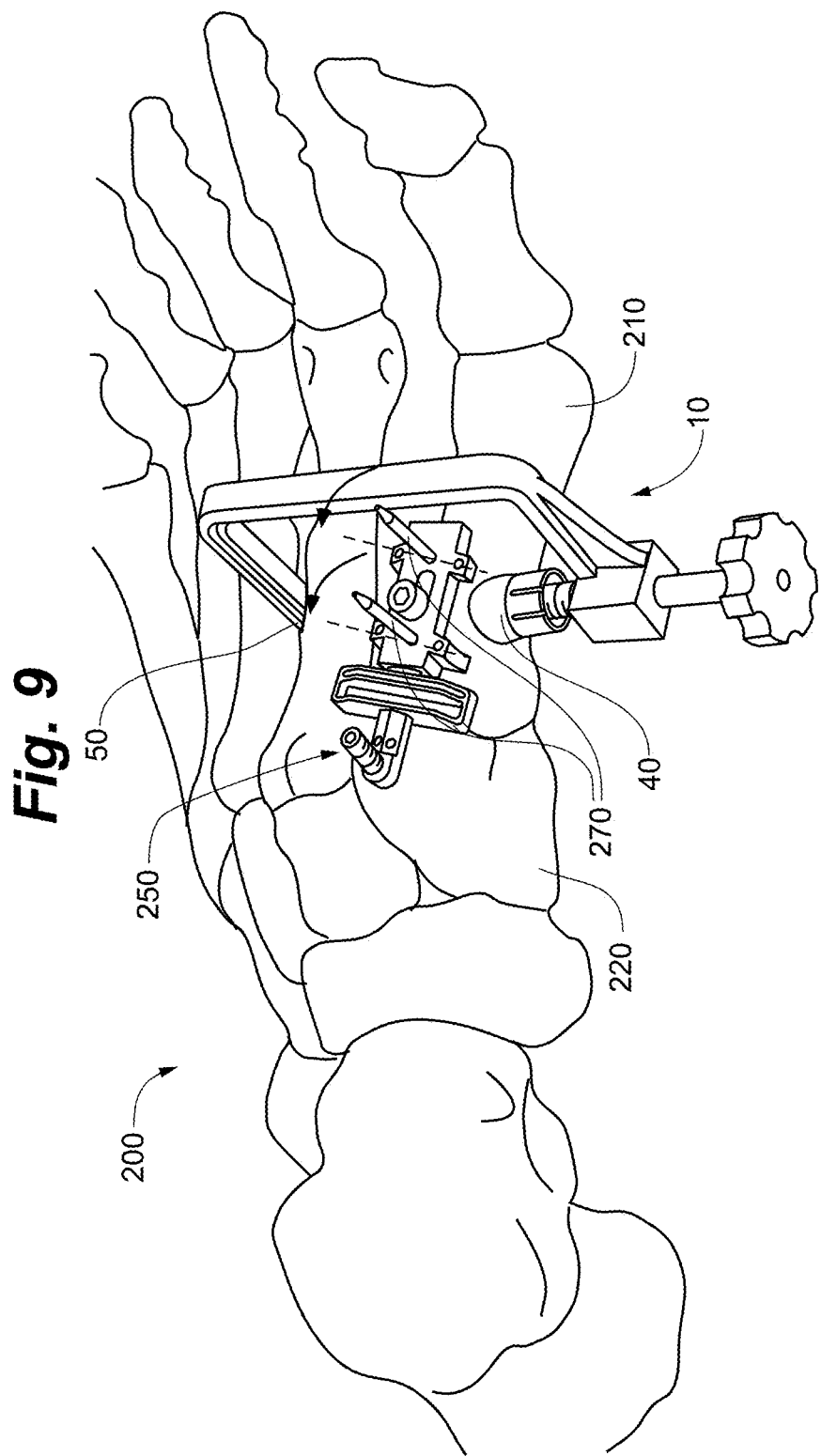
FIG. 9 is a perspective view of a bone cutting guide and a bone positioning guide on a foot depicting a bone adjustment in accordance with an embodiment of the invention.

Also shown in FIG. 7, a bone positioning guide 10 can be attached to the first metatarsal 210 and adjacent second metatarsal 292 (e.g., by installing the bone positioning guide over the top of the cutting guide 250). In some examples, a concave surface of a bone engagement member 40 can be placed in apposition to a medial surface of the first metatarsal 210 and a tip 50 can be placed in apposition to a lateral side of a different metatarsal, such as a second metatarsal 292. FIG. 8 shows repositioning of the first metatarsal 210 with respect to the second metatarsal 292 by moving the bone engagement member 40 with respect to the tip 50 to correct a transverse plane deformity. FIG. 9 shows rotation of the first metatarsal 210 with respect to the bone engagement member 40 to correct a frontal plane deformity. In some embodiments, the fixation pins 270 can be used to impart rotational force to the first metatarsal 210, e.g., by the clinician grasping one or more of the pins and using the pins to physically manipulate the position of the first metatarsal 210. The bone positioning guide 10 can hold the desired position of the first metatarsal.

Figure 10:
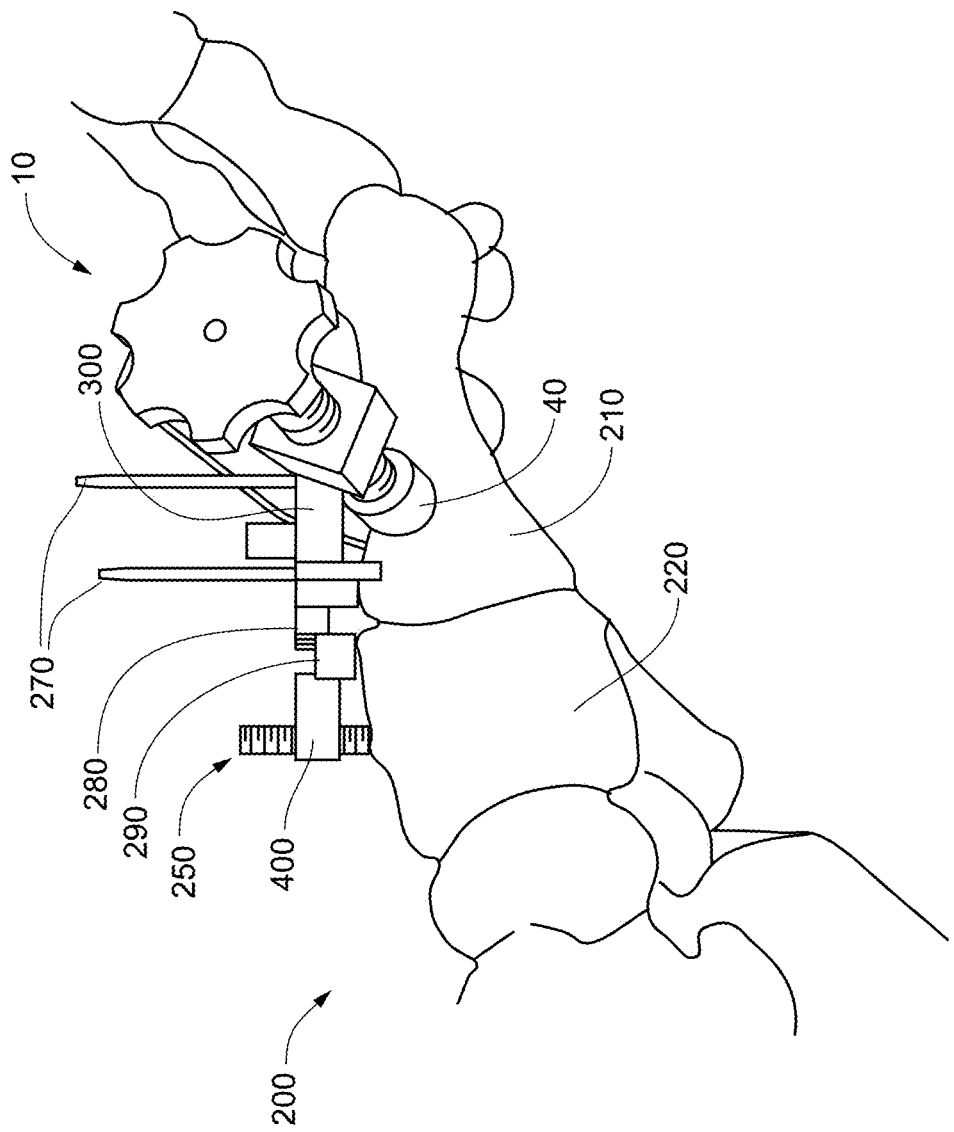
FIG. 10 is a perspective view of a bone cutting guide and a bone positioning guide on a foot positioned for a second bone cut in accordance with an embodiment of the invention.
Figure 11:
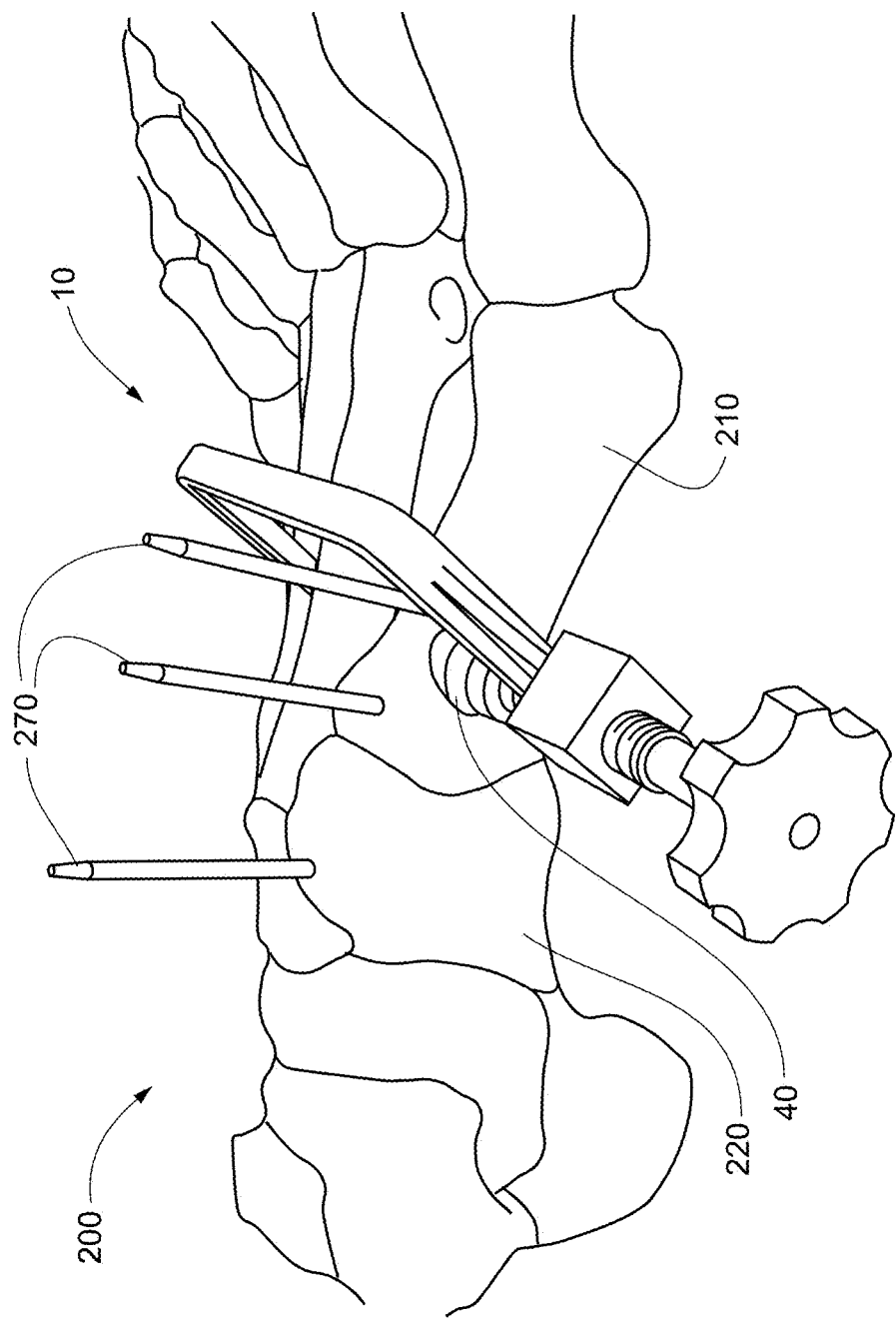
FIG. 11 is a perspective view of a bone positioning guide on a foot in accordance with an embodiment of the invention.
Figure 12:
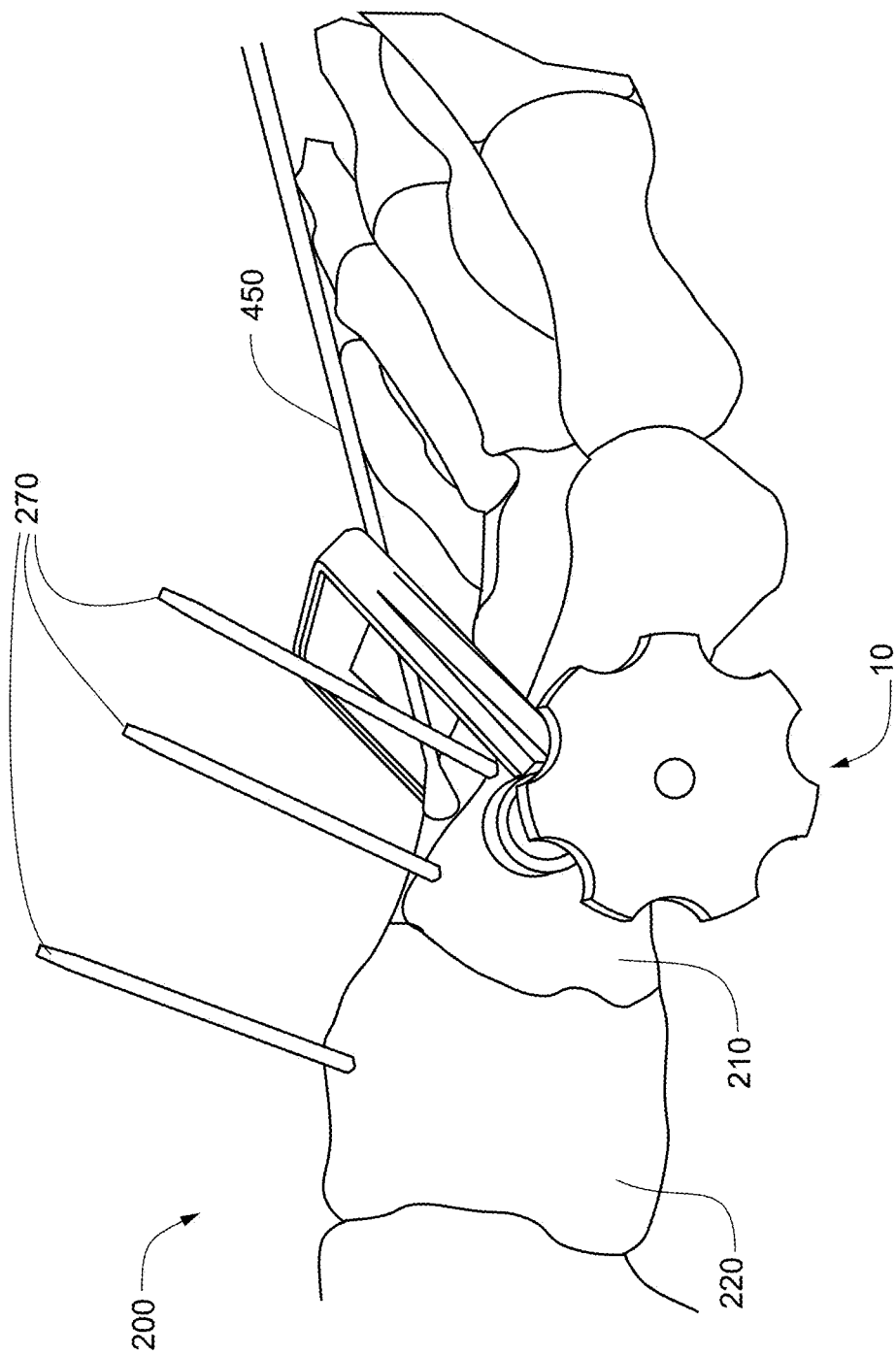
FIG. 12 is a side perspective view of a bone positioning guide on a foot depicting an olive pin providing compression between first and second bones in accordance with an embodiment of the invention.
Figure 13:
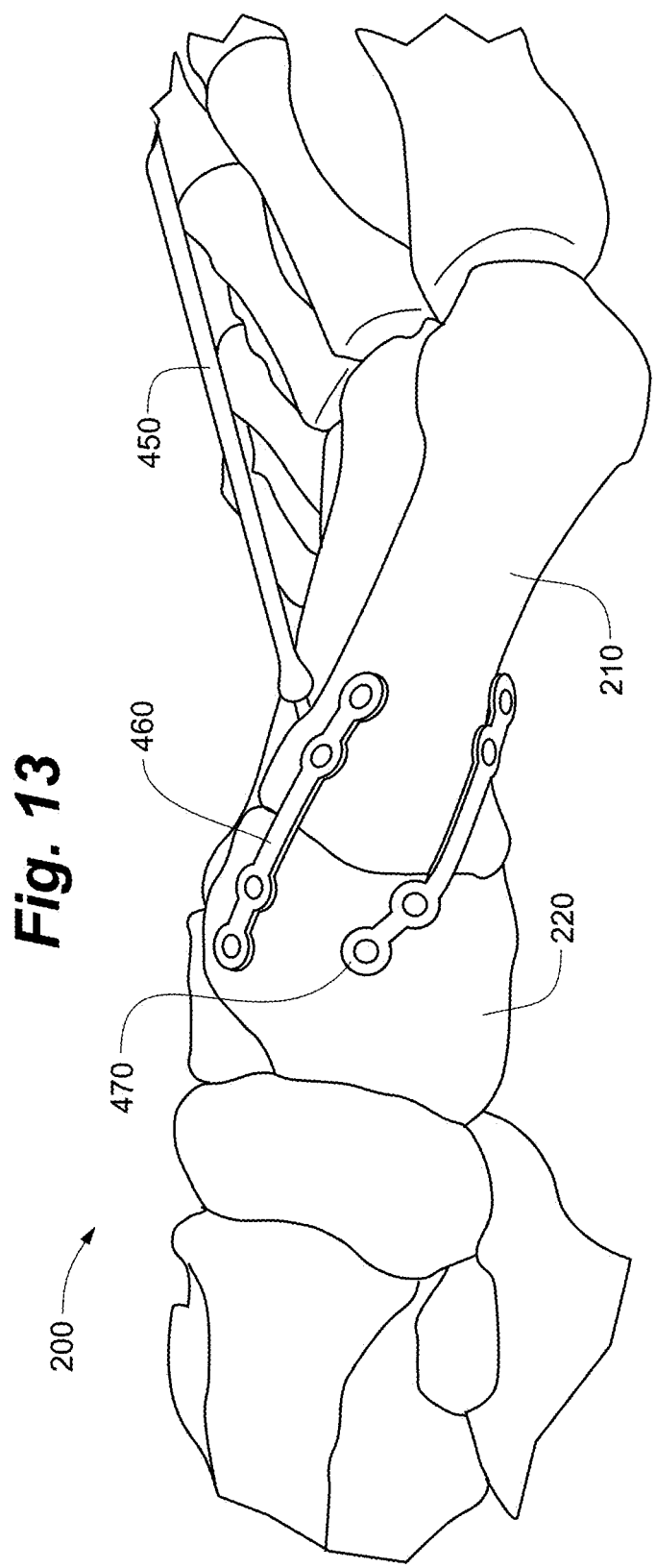
FIG. 13 is a side perspective view of a foot depicting bone plates across a joint between first and second bones in accordance with an embodiment of the invention.

As shown in FIG. 10, the main guide member 280 can be extended from the support 300 to make a parallel cut in the first cuneiform 220. Additional fixation pins 270 can be inserted through apertures in the anchor 400 to fix the cutting guide 250 to the first cuneiform 220. A section of the cuneiform can be cut with a cutting member inserted through the main guide member 280 and removed. In some embodiments the cuneiform cut and the metatarsal cut are parallel, conforming cuts. As shown in FIG. 11, the cutting guide 250 can then be removed with the bone positioning guide 10 in place. FIG. 12 depicts a threaded olive pin 450 inserted through the first metatarsal 210 and into the first cuneiform 220 to provide compression between the first metatarsal and the first cuneiform. The bone positioning guide may then be removed. The position of the bones can then be fixed with a bone screw and/or one or more bone plates of any shape. FIG. 13 shows a first bone plate 460 (e.g., a straight or curved bone plate positioned on a dorsal-medial side) and a second bone plate 470 (e.g., a helical bone plate positioned from a medial side of the cuneiform to a plantar side of the metatarsal (other embodiments, not shown, may include a second straight or curved bone plate)) across the joint space. After the screws are inserted and/or the plates are applied with the insertion of bone screws, the fixation and olive pins may be removed.

Additional details on example surgical technical techniques that can be performed using a bone cutting guide in accordance with the disclosure, as well as details on example features that can be used in conjunction with such bone cutting guide, are described in U.S. patent application Ser. No. 14/981,335, entitled "BONE POSITIONING AND PREPARING GUIDE SYSTEMS AND METHODS" and filed on Dec. 28, 2015, and U.S. patent application Ser. No. 14/990,368, entitled "BONE PLATING SYSTEM AND METHOD" and filed on Jan. 7, 2016, the entire contents of both of which are incorporated herein by reference.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A bone cutting guide for a metatarsal realignment procedure, the bone cutting guide comprising:
   a support sized to be positioned along a length of a metatarsal, the support defining an inner cavity;
   a shaft disposed at least partially within the inner cavity, wherein the shaft is translatable in a distal direction away from the support and a proximal direction toward the support; and
   a main guide member located along the shaft, wherein the main guide member defines a first guide surface defining a first plane and a viewing window located distally of the first guide surface, the viewing window being configured to provide a visual path to a bone being cut using the first guide surface,
   wherein the shaft is configured to translate from a first position that positions the first guide surface over the metatarsal for cutting an end of the metatarsal to a second position that positions the first guide surface over an opposing cuneiform for cutting an end of the opposing cuneiform.

2. The bone cutting guide of claim 1, further comprising a spacer engageable with the main guide member.

3. The bone cutting guide of claim 1, further comprising an anchor translatable with the shaft on a side of the main guide member opposite the support, the anchor comprising at least one fixation aperture for receiving at least one fixation pin to anchor the bone cutting guide to the opposing cuneiform.

4. The bone cutting guide of claim 3, further comprising a first adjustable stabilization screw engaged with the support and a second adjustable stabilization screw engaged with the anchor.

5. The bone cutting guide of claim 3, further comprising at least one fixation aperture extending through the support, wherein at least one fixation pin is configured to extend through the at least one fixation aperture to fixate the support.

6. The bone cutting guide of claim 1, wherein the main guide member includes a second guide surface defining a second plane.

7. The bone cutting guide of claim 1, wherein the second plane is parallel to the first plane.

8. The bone cutting guide of claim 1, further comprising a slot formed on and/or through at least a portion of the support and a securing component positioned at least partially within the slot, the securing component being configured to bear against the shaft to prevent the shaft from traveling within the inner cavity.

9. The bone cutting guide of claim 8, wherein the securing component is configured to translate along the slot relative to the support.

10. A bone cutting guide for a metatarsal realignment procedure, the bone cutting guide comprising:
a support sized to be positioned along a length of a metatarsal, the support defining an inner cavity;
a shaft disposed at least partially within the inner cavity, wherein the shaft is translatable in a distal direction away from the support and a proximal direction toward the support';
a main guide member located along the shaft, wherein the main guide member defines a first guide surface defining a first plane and a viewing window located distally of the first guide surface, the viewing window being configured to provide a visual path to a bone being cut using the first guide surface;
an anchor translatable with the shaft on a side of the main guide member opposite the support; and
a first adjustable stabilization screw engaged with the support; and
a second adjustable stabilization screw engaged with the anchor,
wherein the shaft is configured to translate from a first position that positions the first guide surface over the metatarsal for cutting an end of the metatarsal to a second position that positions the first guide surface over an opposing cuneiform for cutting an end of the opposing cuneiform, and
the anchor comprising at least one fixation aperture for receiving at least one fixation pin to anchor the bone cutting guide to the opposing cuneiform.

11. The bone cutting guide of claim 10, wherein the main guide member further comprises a second guide surface defining a second plane.

12. The bone cutting guide of claim 11, wherein the second plane is parallel to the first plane.

13. The bone cutting guide of claim 10, further comprising a slot formed on and/or through at least a portion of the support and a securing component positioned at least partially within the slot, the securing component being configured to bear against the shaft to prevent the shaft from traveling within the inner cavity.

14. The bone cutting guide of claim 13, wherein the securing component is configured to translate along the slot relative to the support.

* * * * *